US008840659B2

(12) United States Patent
Roeder et al.

(10) Patent No.: US 8,840,659 B2
(45) Date of Patent: *Sep. 23, 2014

(54) STENT AND STENT-GRAFT DESIGNS

(75) Inventors: Blayne A. Roeder, Lafayette, IN (US);
Erik E. Rasmussen, Slagelse (DE);
Sharath Gopalakrishnamurthy,
Bangalore (IN); William K. Dierking,
Louisville, KY (US)

(73) Assignee: Cook Medical Technologies LLC,
Bloomington, IN (US)

( * ) Notice: Subject to any disclaimer, the term of this patent is extended or adjusted under 35 U.S.C. 154(b) by 58 days.

This patent is subject to a terminal disclaimer.

(21) Appl. No.: 13/450,702

(22) Filed: Apr. 19, 2012

(65) Prior Publication Data

US 2012/0277848 A1    Nov. 1, 2012

Related U.S. Application Data

(60) Provisional application No. 61/480,107, filed on Apr. 28, 2011, provisional application No. 61/569,590, filed on Dec. 12, 2011.

(51) Int. Cl.
*A61F 2/82* (2013.01)

(52) U.S. Cl.
USPC ........................................... 623/1.36

(58) Field of Classification Search
USPC .............................. 623/1.15–1.42
See application file for complete search history.

(56) References Cited

U.S. PATENT DOCUMENTS

| 5,383,887 | A | * | 1/1995 | Nadal ........................... 606/200 |
| 5,562,724 | A | | 10/1996 | Vorwerk et al. |
| 5,720,776 | A | | 2/1998 | Chuter et al. |
| 6,004,347 | A | | 12/1999 | McNamara et al. |
| 6,099,558 | A | | 8/2000 | White et al. |
| 6,102,940 | A | | 8/2000 | Robichon et al. |
| 6,123,722 | A | | 9/2000 | Fogarty et al. |
| 6,368,345 | B1 | | 4/2002 | Dehdashtian et al. |
| 6,652,580 | B1 | | 11/2003 | Chuter et al. |

(Continued)

FOREIGN PATENT DOCUMENTS

| FR | 2747912 | 10/1997 |
| WO | WO2011/031981 | 3/2011 |

OTHER PUBLICATIONS

Extended European Search Report for 12275049.0 dated Aug. 31, 2012, 6 pgs.

(Continued)

*Primary Examiner* — Suzette J Gherbi
(74) *Attorney, Agent, or Firm* — Brinks Gilson & Lione

(57) ABSTRACT

The present embodiments provide stents and stent-grafts for use in medical procedures. In one embodiment, a stent comprises a series of proximal apices, a series of distal apices, and at least one imaging element. A distal region of the stent, including the series of distal apices and a first suture bore, overlaps with the graft material, while a proximal region of the stent, including the series of proximal apices and at least one barb, is disposed proximally beyond the graft material. In an alternative embodiment, a stent-graft comprises a graft, a first stent and a second stent, in which a series of proximal apices of the first stent are each disposed distal to the proximal end of the graft, and a series of proximal apices of the second stent are each disposed proximally beyond the proximal end of the graft.

15 Claims, 11 Drawing Sheets

(56) References Cited

U.S. PATENT DOCUMENTS

| | | | |
|---|---|---|---|
| 6,730,117 B1* | 5/2004 | Tseng et al. | 623/1.16 |
| 6,884,260 B2* | 4/2005 | Kugler et al. | 623/1.15 |
| 7,147,660 B2 | 12/2006 | Chobotov et al. | |
| 7,175,652 B2 | 2/2007 | Cook et al. | |
| 7,226,474 B2 | 6/2007 | Iancea et al. | |
| 7,615,072 B2 | 11/2009 | Rust et al. | |
| 7,637,932 B2 | 12/2009 | Bolduc et al. | |
| 7,655,034 B2 | 2/2010 | Mitchell et al. | |
| 7,666,221 B2 | 2/2010 | Escano | |
| 7,708,771 B2* | 5/2010 | Chuter et al. | 623/1.13 |
| 7,763,063 B2 | 7/2010 | Arbefeuille et al. | |
| 7,998,194 B2* | 8/2011 | Pollock et al. | 623/1.36 |
| 8,163,007 B2* | 4/2012 | Dierking et al. | 623/1.36 |
| 8,211,160 B2 | 7/2012 | Garrison et al. | |
| 2005/0075728 A1* | 4/2005 | Nguyen et al. | 623/2.17 |
| 2005/0137701 A1* | 6/2005 | Salahieh et al. | 623/2.38 |
| 2005/0172471 A1* | 8/2005 | Vietmeier | 29/447 |
| 2006/0004436 A1* | 1/2006 | Amarant et al. | 623/1.15 |
| 2006/0195172 A1 | 8/2006 | Luo et al. | |
| 2006/0259123 A1 | 11/2006 | Dorn | |
| 2007/0055345 A1 | 3/2007 | Arbefeuille | |
| 2007/0219620 A1 | 9/2007 | Eells et al. | |
| 2007/0239267 A1 | 10/2007 | Hendriks et al. | |
| 2008/0154356 A1* | 6/2008 | Obermiller et al. | 623/1.26 |
| 2008/0208312 A1 | 8/2008 | Kwitkin et al. | |
| 2008/0255655 A1 | 10/2008 | Kusleika et al. | |
| 2009/0069880 A1 | 3/2009 | Vonderwalde et al. | |
| 2009/0082846 A1 | 3/2009 | Chobotov | |
| 2009/0125096 A1* | 5/2009 | Chu et al. | 623/1.14 |
| 2009/0164001 A1 | 6/2009 | Biggs et al. | |
| 2009/0204202 A1* | 8/2009 | Dierking et al. | 623/1.16 |
| 2009/0234429 A1* | 9/2009 | Lau | 623/1.12 |
| 2010/0010622 A1* | 1/2010 | Lowe et al. | 623/1.16 |
| 2010/0161028 A1* | 6/2010 | Chuter et al. | 623/1.13 |
| 2010/0168841 A1 | 7/2010 | Furst et al. | |
| 2010/0191320 A1* | 7/2010 | Straubinger et al. | 623/1.15 |
| 2010/0211161 A1 | 8/2010 | Dreher | |
| 2010/0268326 A1 | 10/2010 | Leynov et al. | |
| 2010/0274349 A1 | 10/2010 | Lord et al. | |
| 2010/0286757 A1 | 11/2010 | Petersen et al. | |
| 2010/0292777 A1* | 11/2010 | Meyer et al. | 623/1.16 |
| 2011/0270380 A1 | 11/2011 | Bruszewski | |
| 2012/0277848 A1* | 11/2012 | Roeder et al. | 623/1.13 |
| 2012/0296416 A1 | 11/2012 | Garrison et al. | |
| 2013/0238084 A1 | 9/2013 | Bales, Jr. et al. | |
| 2013/0289220 A1* | 10/2013 | Cottone | 525/439 |
| 2013/0331926 A1 | 12/2013 | Wu | |

OTHER PUBLICATIONS

Response to Extended European Search Report for 12275049.0 filed Apr. 26, 2013, 13 pgs.
Corrected Response to Extended European Search Report for 12275049.0 filed May 3, 2013, 5 pgs.
Patent Examination Report No. 1 for Australian Patent Application No. 2012202376 dated Feb. 21, 2013, 3 pgs.
Response to Patent Examination Report No. 1 for Australian Patent Application No. 2012202376 filed Feb. 6, 2014, 8 pgs.
Patent Examination Report No. 2 for Australian Patent Application No. 2012202376 dated Mar. 7, 2014, 3 pgs.
Office Action dated Jun. 13, 2014 for U.S. Appl. No. 14/056,502, 9 pgs.

* cited by examiner

STENT AND STENT-GRAFT DESIGNS

PRIORITY CLAIMS

This application claims the benefit of priority of U.S. Provisional Application Ser. No. 61/480,107, entitled "Stent Designs For Use With One Or More Trigger Wires," filed Apr. 28, 2011, and also claims the benefit of priority of U.S. Provisional Application Ser. No. 61/569,590, entitled "Stent Designs For Use With One Or More Trigger Wires," filed Dec. 12, 2011, the disclosures of which are both hereby incorporated by reference in their entireties.

BACKGROUND

The present embodiments relate generally to apparatus and methods for treating medical conditions, and more specifically, to stents and stent-grafts for use in body vessels to treat those medical conditions.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs, such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices formed beneath the proximal and/or distal apices, e.g., a location where an individual apex splits into two separate strut segments.

If trigger wires are threaded through the vertices of such cannula-cut stents, the trigger wires may become crimped at the vertices during compression of the stent to a reduced diameter delivery profile. If the trigger wires are crimped between the strut segments, the trigger wires and/or stent segments may become damaged during delivery, particularly for nickel-titanium stents that may be sensitive to surface imperfections. Furthermore, when compressing a cannula-cut stent having relatively acute bends to a significantly reduced radial profile, barbs disposed near the apices of the stent may become entangled with the stent struts and/or the trigger wires.

SUMMARY

The present embodiments provide stents and stent-grafts for use in medical procedures.

In one embodiment, a stent for use in a medical procedure comprises a series of proximal apices disposed at a proximal end of the stent and a series of distal apices disposed at a distal end of the stent. A plurality of strut segments are disposed between the series of proximal apices and the series of distal apices, where the strut segments enable expansion of the stent from a compressed state to a deployed state. At least one barb is disposed at a location between the series of proximal apices and the series of distal apices. Further, an imaging element is disposed at a location distal to the at least one barb, and a first suture bore is disposed in a surface of the stent at a location distal to the imaging bore. A distal region of the stent, including the series of distal apices and the first suture bore, overlaps with a graft material, while a proximal region of the stent, including the series of proximal apices and the at least one barb, is disposed proximally beyond the graft material.

In one example, the distal region of the stent that overlaps with the graft material accounts for between about 20 to about 45 percent of the longitudinal length of the stent, while the proximal region that is disposed distally beyond the graft material accounts for between about 55 to about 80 percent of the longitudinal length of the stent. Further, the imaging bore may be disposed at the location corresponding to an endpoint of a proximal edge of the graft material.

In various embodiments, the stents described herein advantageously may reduce the number of trigger wires required during delivery, as a single trigger wire is not needed to restrain each individual apex. In one example, the series of proximal apices comprise alternating first and second proximal apices, where each of the first proximal apices comprises an end region having a first bore, and where each of the second proximal apices comprises a second bore, where at least one of the first proximal apices is simultaneously restrained with an adjacent, second proximal apex by a single trigger wire during delivery of the stent. The first bore formed in the first proximal apex may directly overlap with the second bore in the second proximal apex in a delivery state, where a single trigger wire is configured to be simultaneously disposed through the first and second bores.

In an alternative embodiment, a stent-graft for use in a medical procedure comprises a graft, a first stent and a second stent. The first stent has a plurality of strut segments disposed between a series of proximal and distal apices, and overlaps with the graft such that the series of proximal apices are each disposed distal to a proximal end of the graft. The second stent has a plurality of strut segments disposed between a series of proximal apices and a series of distal apices, where the series of distal apices of the second stent are each disposed distal to the proximal end of the graft, and the series of proximal apices of the second stent are each disposed proximally beyond the proximal end of the graft.

In various alternative embodiments, at least one of the proximal apices of the first stent may be circumferentially aligned with a corresponding distal apex of the second stent.

At least one of the proximal apices of the first stent may be sutured to one of the distal apices of the second stent. The first stent and the second stent may comprise different geometries.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
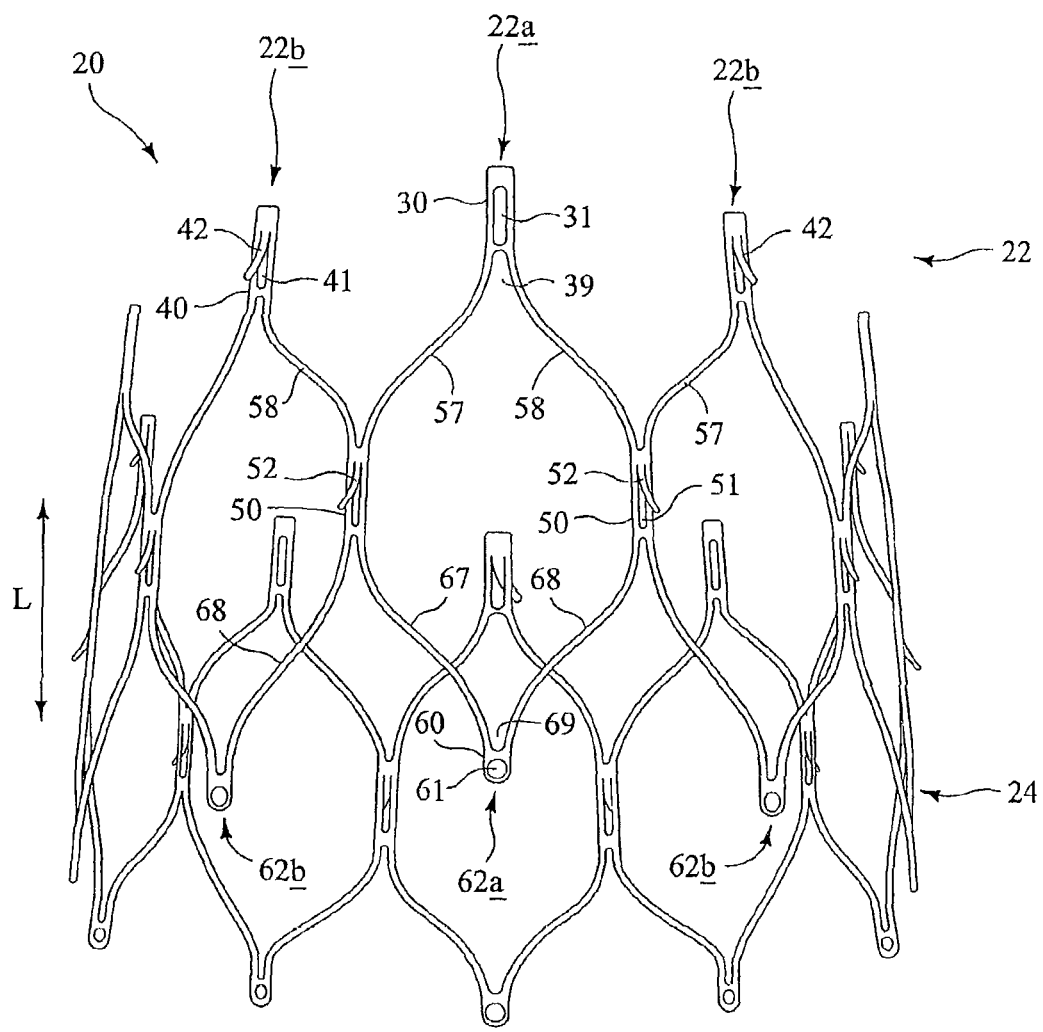
FIG. 1 is a lower perspective view of an exemplary cannula-cut stent.

Referring to FIG. 1, a stent 20 may be manufactured from a continuous cylinder into which a pattern may be cut by a laser or by chemical etching to produce slits in the wall of the cylinder. The resulting structure may then be heat set to give it a desired final configuration. The preferred final configuration includes a shape having a series of proximal apices and a series of distal apices, as generally shown in FIG. 1. Therefore, the proximal end 22 of the stent 20 may comprise multiple adjacent proximal apices 22a and 22b, while the distal end 24 of the stent 20 may comprise multiple adjacent distal apices 62a and 62b, as shown in FIG. 1.

In previously-known stents, one or more trigger wires may have been disposed through a vertex 39 at the proximal end 22 and/or through a vertex 69 at the distal end 24 of the stent. When the stent is compressed for delivery, if a trigger wire was disposed through the vertices 39 and 69, the trigger wire may become pinched against the struts of the stent, which may damage the stent struts and/or the trigger wire itself. As explained below, the present embodiments utilize a different approach to coupling one or more trigger wires to the stent 20.

Figure 2:
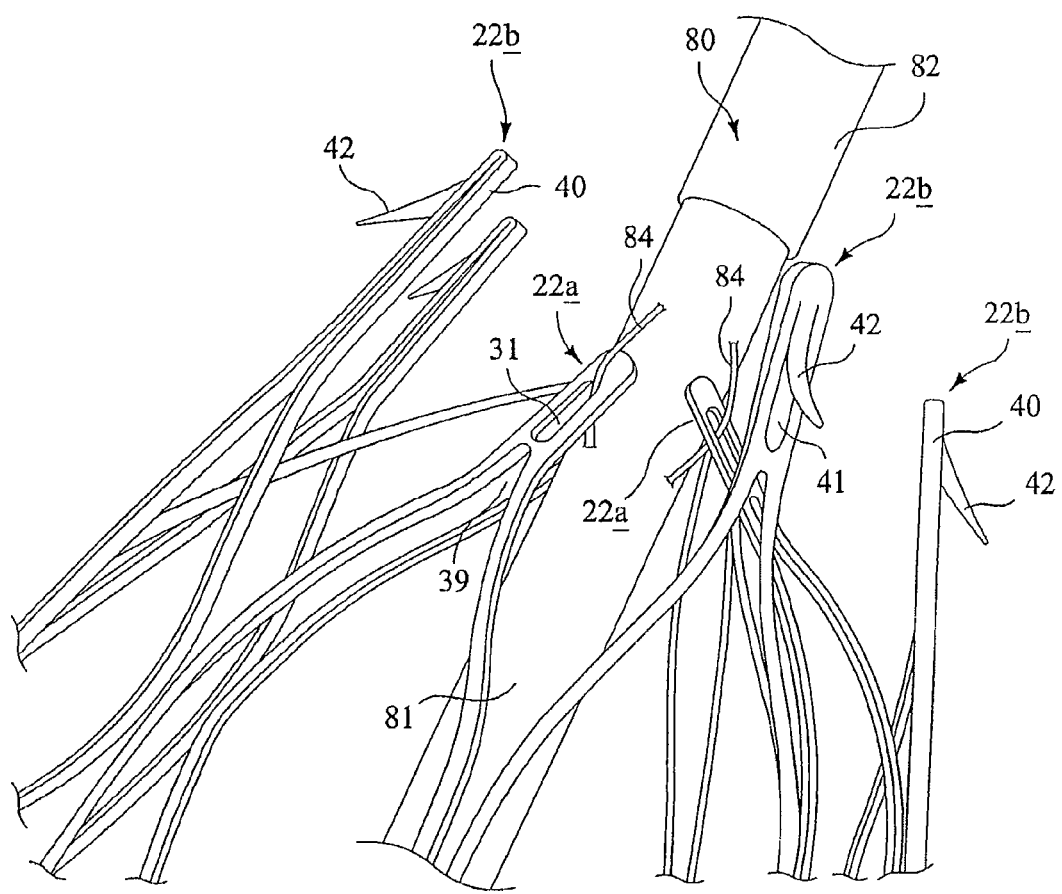
FIG. 2 is a perspective view illustrating the attachment of the stent of FIG. 1 to a delivery system.

Referring still to FIGS. 1-2, at least one pair of adjacent, proximal apices 22a and 22b comprises different features. For example, as shown in FIG. 2, a first proximal apex 22a may comprise an end region 30 having a bore 31 formed therein, wherein the bore 31 is configured to receive a trigger wire 84. A second, adjacent proximal apex 22b comprises an end region 40 having an integral barb 42 formed therein, as shown in FIGS. 1-2. However, the second proximal apex 22b is not configured to be restrained using a trigger wire, as explained and shown in FIG. 2 below. By using adjacent proximal apices 22a and 22b having the different features shown herein, an improved trigger wire attachment may be achieved and barb entanglement may be reduced, as explained further below.

As noted above, the stent 20 may comprise one or more barbs 42 disposed in at least one of the end regions 40 of the second proximal apices 22b. The barbs 42 may be formed by laser cutting a desired barb shape into the end regions 40. A slit 41 therefore is formed into each end region 40 after the desired barb shape is formed, as shown in FIGS. 1-2. Once the desired barb shape is cut, a main body of the barb 42 may be bent in a radially outward direction with respect to the end region 40. The angle may comprise any acute angle, or alternatively may be substantially orthogonal or obtuse. If desired, the barbs 42 may be sharpened, for example, by grinding the tip of the barb, to facilitate engagement at a target tissue site.

Referring still to FIG. 1, the stent 20 may comprise at least one strut segment disposed between the proximal and distal apices. For example, multiple angled strut segments may be disposed between a first proximal apex 22a and a corresponding distal apex 62a, and an identical set of angled strut segments may be disposed between an adjacent, second proximal apex 22b and a corresponding distal apex 62b. By way of example, the first proximal apex 22a extends distally and splits into first and second angled strut segments 57 and 58, respectively, thereby forming a proximal vertex 39, as shown in FIG. 1. In a compressed state, the first and second angled strut segments 57 and 58 may be compressed such that they are substantially parallel to one another. In the expanded state shown in FIG. 1, the first and second angled strut segments 57 and 58 are disposed an angle relative to a longitudinal axis L of the stent 20. In the expanded state, the first and second angled strut segments 57 and 58 may be disposed at an angle of about 20-60 degrees relative to the longitudinal axis L of the stent 20, as depicted in FIG. 1.

Similarly, each distal apex 62a may extend in a proximal direction and splits into first and second angled strut segments 67 and 68, respectively, thereby forming a distal vertex 69. The first angled strut segments 57 and 67 of the proximal and distal apices 22a and 62a, respectively, may meet with the second angled strut segments 58 and 68 of the adjacent proximal and distal apices 22b and 62b, respectively, thereby forming a transition region 50. In this manner, the stent 20 may be formed into a continuous, generally cylindrical shape, as shown in FIG. 1.

Expansion of the stent 20 is at least partly provided by the angled strut segments 57, 58, 67 and 68, which may be substantially parallel to one another in a compressed state, but may tend to bow outward away from one another in the expanded state shown in FIG. 1. As explained further below, the stent 20 may be formed from any suitable material, and preferably a laser-cut nitinol cannula. If manufactured from nitinol, the stent 20 may assume the expanded state shown in FIG. 1 upon removal of a delivery sheath.

Each transition region 50 may be oriented in a direction that is substantially parallel to the longitudinal axis L of the stent 20, as shown in FIG. 1. Further, each transition region 50 may comprise a larger surface area relative to the angled segments, since the transition regions may be composed substantially of multiple different angled segments 57, 58, 67 and 68 meeting at a central location.

Referring still to FIG. 1, the stent 20 may comprise at least one barb 52 disposed in at least one of the transition regions 50. The barb 52 may be formed integrally, as part of the strut, or may comprise an external barb that is adhered to a surface of the transition regions 50. Preferably, as shown in FIG. 1, multiple integral barbs 52 are provided. The barbs 52 may be formed by laser cutting a desired barb shape into the transition regions 50. In this manner, the barbs are monolithic with the transition region 50. A slit 51 therefore is formed into the transition region 50 after the desired barb shape is formed, as shown in FIG. 1. Since the transition regions 50 may comprise an increased surface area relative to other regions of the stent 20, it may be easier to perforate portions of the transition regions 50 without adversely affecting the structural integrity of the stent. Once the desired barb shape is cut, a main body of the barb 52 may be bent in an outward direction at any angle with respect to the transition region 50 and optionally may be sharpened to facilitate engagement at a target tissue site.

Each of distal apices 62a and 62b may comprise an end region 60 having a bore 61 formed therein, as shown in FIG. 1. The distal end 24 of the stent 20 may be coupled to a proximal end of graft material, such as the graft material 300 of FIG. 9 below. The distal apices 62a and 62b may be coupled to the graft material, for example, using one or more sutures that are looped through the graft material and the bores 61 of the stent 20. In this manner, the stent 20 may be used as an attachment stent for endovascular graft fixation. For example, the graft material may overlap with an aneurysm to seal off fluid flow into the aneurysm, while the proximal end 22 of the stent 20 may extend in a proximal direction away from the graft material, e.g., to engage a healthy portion of a vessel wall away from a diseased portion of the aneurysm.

The stent 20 has a reduced diameter delivery state so that it may be advanced to a target location within a vessel or duct. The stent 20 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 20. Further, the struts of the stent 20 may comprise a substantially flat wire profile or may comprise a rounded profile. As best seen in FIG. 2, the struts of the stent 20 generally comprise a flat wire profile.

The stent 20 may be manufactured from a super-elastic material. Solely by way of example, the super-elastic material may comprise a shape-memory alloy, such as a nickel titanium alloy (nitinol). If the stent 20 comprises a self-expanding material such as nitinol, the stent may be heat-set into the desired expanded state, whereby the stent 20 can assume a relaxed configuration in which it assumes the preconfigured first expanded inner diameter upon application of a certain cold or hot medium. Alternatively, the stent 20 may be made from other metals and alloys that allow the stent 20 to return to its original, expanded configuration upon deployment, without inducing a permanent strain on the material due to compression. Solely by way of example, the stent 20 may comprise other materials such as stainless steel, cobalt-chrome alloys, amorphous metals, tantalum, platinum, gold and titanium. The stent 20 also may be made from non-metallic materials, such as thermoplastics and other polymers.

Referring now to FIG. 2, the stent 20 may be delivered to a target site in a compressed configuration using a pushing member 80 and a plurality of trigger wires 84. In FIG. 2, the exemplary pushing member 80 comprises a main body 81 and a tapered region 82, which is disposed proximal to the main body 81. The tapered region 82 may subsequently transition into a smaller diameter at a proximal location, such that the relatively small diameter proximal region allows for atraumatic access and delivery. The plurality of trigger wires 84 may be disposed within the confines of the main body 81, and may span the length of the pushing member 80. The triggers wires 84 also may be activated by manipulating one or more handles, with optional locking features, to control deployment of the proximal end 22 of the stent 20.

A single trigger wire 84 may be looped through the bore 31 of selected ones of the first proximal apices 22a to restrain the stent 20 during delivery. Trigger wires are not coupled to the second proximal apices 22b, which comprise the barbs 42. In the embodiment shown, the trigger wires 84 are only disposed through alternating proximal apices, as seen in FIG. 2. By restraining selected ones of the first proximal apices, such as each first proximal apex 22a, the adjacent second proximal apices 22b also may be indirectly pulled in a radially inward direction during delivery. The configuration of the stent 20, and in particular the angled segments 57, 58, 67 and 68 that meet up at transition regions 50, facilitates the indirect compression of the adjacent second proximal apices 22b. Advantageously, since only selected ones of the proximal apices are restrained during delivery, the number of trigger wires may be reduced. Moreover, since the barbs 42 are only disposed on every other apex, barb entanglement may be reduced or eliminated, as depicted in FIG. 2.

Another advantage associated with the design of the stent 20 is that the trigger wires 84 are only disposed through the bores 31 of the first proximal apices 22a, as opposed to being disposed through the vertices 39. Therefore, the trigger wires 84 may be less likely to become damaged during compression of the stent 20. Further, the stent struts themselves are less likely to become damaged since the trigger wires 84 are isolated within the bores 31 of the first proximal apices 22a.

Figure 3:
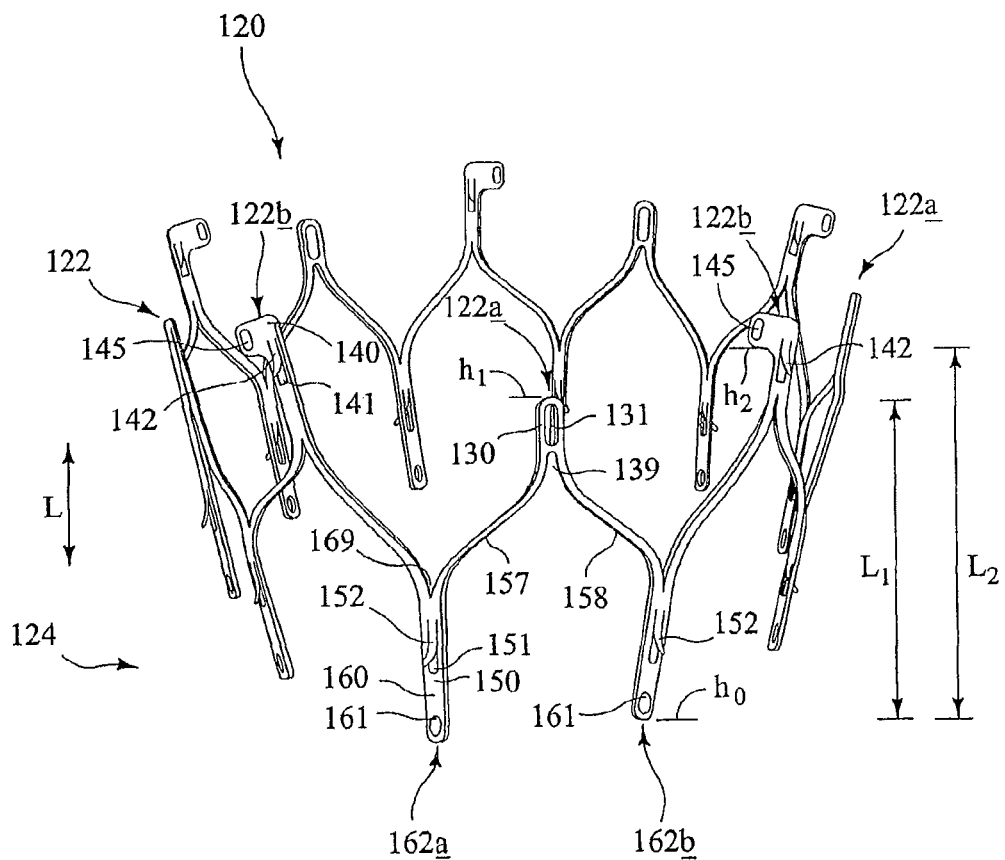
FIG. 3 is an upper perspective view of another exemplary stent.

Referring now to FIGS. 3-6, an alternative stent design is described. In FIG. 3, stent 120 also may be manufactured from a continuous cylinder into which a pattern may be cut by a laser or by chemical etching to produce slits in the wall of the cylinder. The resulting structure may thereafter be heat set to give it a desired final configuration. The preferred final configuration includes a shape having a series of proximal apices and a series of distal apices, as generally shown in FIG. 3. Therefore, the proximal end 122 of the stent 120 may comprise multiple adjacent proximal apices 122a and 122b, while the distal end 124 of the stent 20 may comprise multiple adjacent distal apices 162a and 162b, as shown in FIG. 3.

Figure 4:
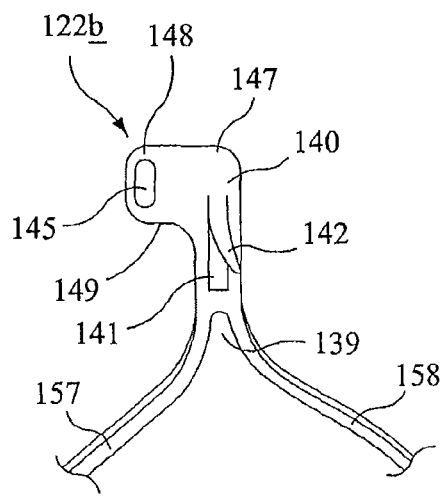
FIG. 4 is a perspective view illustrating features of a proximal apex of the stent of FIG. 3.
Figure 5:
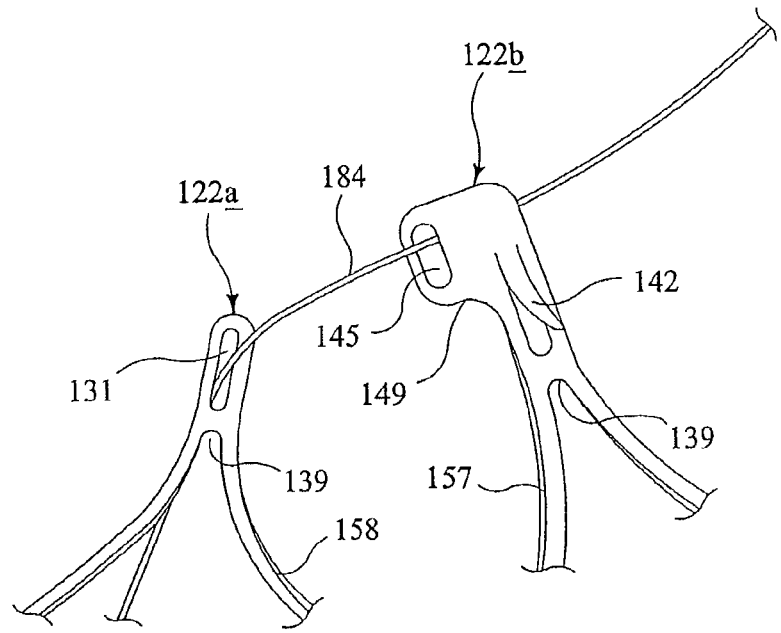
FIG. 5 is a perspective view showing a trigger wire coupled to adjacent proximal apices of the stent of FIGS. 3-4.
Figure 6:
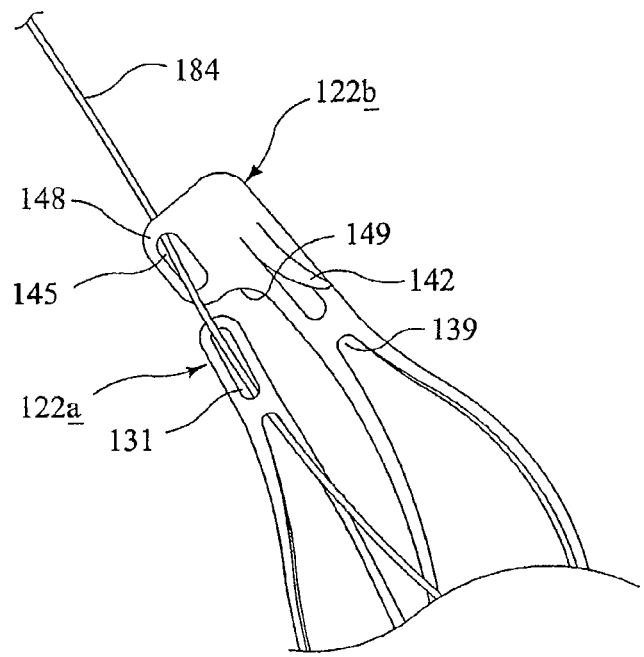
FIG. 6 is a perspective view showing the trigger wire of FIG. 5 holding the stent in a delivery configuration.

One or more pairs of adjacent, proximal apices 122a and 122b may comprise different features. For example, a first proximal apex 122a may comprise an end region 130 having a first bore 131 formed therein, wherein the first bore 131 is configured to receive a trigger wire 184, as shown in FIGS. 5-6 below. A second, adjacent proximal apex 122b comprises an end region 140 having an integral barb 142 formed therein, as shown in FIGS. 3-6. The second proximal apex 122b further comprises a second bore 145 formed therein, as best seen in FIG. 4, which is configured to receive the same trigger wire 184 as the adjacent first proximal apex 122a, as explained and shown with respect to FIGS. 5-6 below. By using adjacent proximal apices 122a and 122b having the different features shown herein, an improved trigger wire attachment may be achieved and barb entanglement may be reduced, as explained further below.

Each of the second proximal apices 122b may comprise first and second regions 147 and 148, as shown in FIG. 4. A single barb 142 may be disposed in each of the second proximal apices 122b generally in the first region 147, while the second bore 145 may be disposed generally in the second region 148, as shown in FIG. 4. The barbs 142 may be formed by laser cutting a desired barb shape into the end regions 140, thereby forming a slit 141, as generally explained with respect to the stent 20 hereinabove. Once the desired barb shape is cut, a main body of the barb 142 may be bent in a radially outward direction and optionally may be sharpened, as generally set forth above.

The second proximal apices 122b further may comprise a recessed portion 149 formed at a location distal to the second bore 145, as best seen in FIG. 4. As will be explained further below, during delivery of the stent 120, the first proximal apex 122a is configured to be pulled towards the second proximal apex 122b and may become nested within the recessed portion 149 of the second proximal apex 122b when a trigger wire is disposed through the first and second bores 131 and 145.

The first bores 131 of the first proximal apices 122a may be disposed slightly distal to the second bores 145 of an adjacent, second proximal apex 122b. Further, a first longitudinal distance $L_1$ between a distal edge $h_0$ of the stent 120 and a proximal edge $h_1$ of each proximal apex 122a may be less than a second longitudinal distance $L_2$ between the distal edge $h_0$ of the stent and a distal edge $h_2$ of each recessed portion 149, as shown in FIG. 3. This length differentiation may facilitate nesting of the first proximal apices 122a within the recessed portions 149 of the second proximal apices 122b during delivery of the stent, as explained further below with respect to FIGS. 5-6.

Referring still to FIG. 3, the stent 120 may comprise at least one strut segment disposed between the proximal and distal apices. In one configuration, the proximal and distal apices are not directly aligned with one another. For example, as shown in FIG. 3, a first angled segment 157 may be disposed between a proximal apex 122a and a corresponding distal apex 162a, and a second angled segment 158 may be disposed between the same proximal apex 122a and an adjacent distal apex 162b. In effect, each proximal apex 122a and 122b extends distally and splits into the first and second angled strut segments 157 and 158, respectively, thereby forming a proximal vertex 139. Similarly, each distal apex 162a and 162b extends proximally and splits into the first and second angled strut segments 157 and 158, respectively, thereby forming a distal vertex 169. In this manner, the stent 120 may be formed into a continuous, generally cylindrical shape, as shown in FIG. 3.

In a compressed state, the first and second angled strut segments 157 and 158 may be compressed such that they are substantially parallel to one another. In the expanded state shown in FIG. 3, the first and second angled strut segments 157 and 158 may be disposed at an angle relative to a longitudinal axis L of the stent 120, as shown in FIG. 3. In the expanded state, the first and second angled strut segments 157 and 158 may be disposed at an angle of about 20-60 degrees relative to the longitudinal axis L of the stent 120. Expansion of the stent 120 is at least partly provided by the angled strut segments 157 and 158, which may be substantially parallel to one another in a compressed state, but may tend to bow outward away from one another in the expanded state shown in FIG. 3. Like the stent 20 noted above, the stent 120 may be formed from any suitable material, and preferably a nickel-titanium alloy, so that it may assume the expanded state shown in FIG. 3 upon removal of a delivery sheath.

The first and second angled strut segments 157 and 158 meet with one another distally to form a distal transition region 150, which effectively is the same as the distal end region 160 of the stent 120. Each end region 160 may be oriented in a direction that is substantially parallel to the longitudinal axis L of the stent 120, as shown in FIG. 3. Further, each end region 160 may comprise a larger surface area relative to the angled segments, since the end regions 160 are composed substantially of multiple different angled segments 157 and 158 meeting up together. At least one distal barb 152 may be formed integrally by laser cutting a desired barb shape, thereby forming a slit 151 into the end region 160, as shown in FIG. 3. Since the end regions 160 may comprise an increased surface area relative to other regions of the stent 120, it may be easier to perforate portions of the end regions 160 without adversely affecting the structural integrity of the stent. Further, a suture bore 161 may be formed in the end regions 160 of each of the distal apices 162a and 162b, as shown in FIG. 3. The distal end 124 of the stent 120 may be coupled to a proximal end of graft material, such as the graft material 300 of FIG. 9 below, by looping the suture through the bore 161 and the graft material, as generally explained above with respect to the embodiment of FIGS. 1-2.

Referring now to FIGS. 5-6, the stent 120 may be delivered to a target site in a compressed configuration using a pushing member, such as pushing member 80 of FIG. 2, and a plurality of trigger wires. In accordance with one aspect, a trigger wire 184 may be looped through the first bore 131 of each first proximal apex 122a, and further looped through the second bore of an adjacent, second proximal apex 122b. Therefore, each individual trigger wire may restrain two separate, adjacent proximal apices during delivery. When the stent 120 is fully compressed, as depicted in FIG. 6, the adjacent first and second proximal apices 122a and 122b may be pulled closer together in the circumferential direction. Due to the difference between lengths $L_1$ and $L_2$, each proximal apex 122a may become nested substantially within the recessed portion 149 distal to the second region 148 of the proximal apex 122b, as shown in FIG. 6. Further, the first bore 131 may be positioned distal to the second bore 145, such that the first and second bores 131 and 145 are disposed substantially in longitudinal alignment with one another when the single trigger wire 184 is disposed through the first and second bores during delivery of the stent.

Advantageously, one single trigger wire may be used to restrain two separate, adjacent apices of the stent 120. Further, the trigger wires 184 are only disposed through the bores 131 and 145, but not disposed around the vertices 139, and therefore the trigger wires may be less likely to become damaged during compression of the stent 120. Further, the stent struts themselves are less likely to become damaged since the trigger wires 184 are isolated within the bores 131 and 145.

Figure 7:
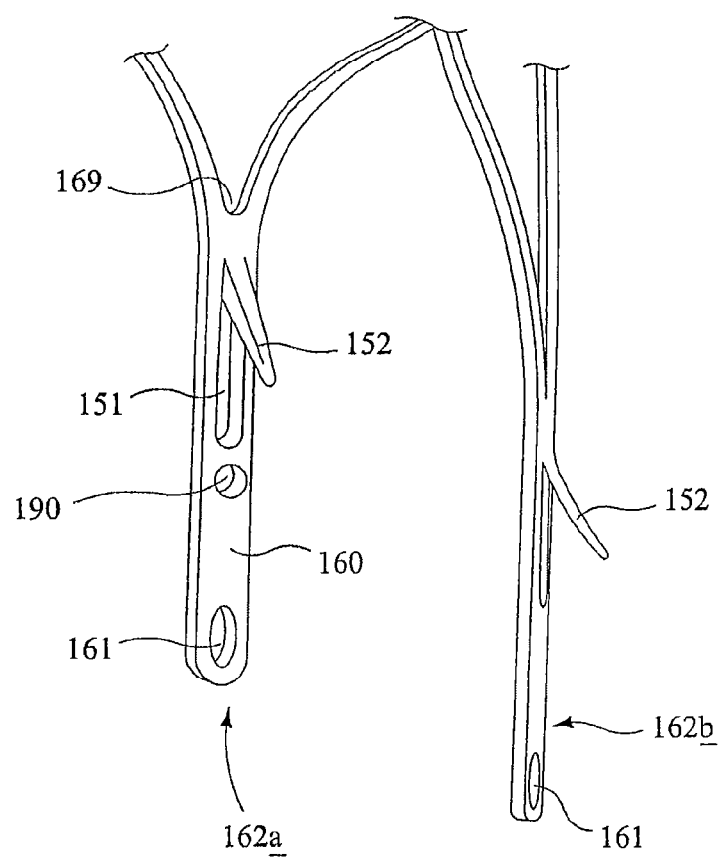
FIG. 7 is a perspective view showing a distal apex having a bore for receiving a radiopaque marker.

Referring now to FIG. 7, one or more of the distal apices 162a and 162b optionally may comprise an imaging bore 190, which may be disposed between the suture bore 161 and the barb slit 151. The imaging bore 190 may receive any suitable radiopaque marker, such as a gold marker. Preferably, the imaging bores 190 and associated radiopaque markers are provided on alternating distal apices, e.g., only distal apices 162a. Alternatively, the imaging bores 190 may be disposed on each distal apex 162a and 162b, or disposed on every third or fourth apex around the perimeter of the stent. The imaging bores 190 may be beveled, or alternatively, may be substantially orthogonal to the strut of the end region 160.

In use, the imaging bores 190 may be aligned with the distal edge of a graft material, for example, when the stent 120 is used for endovascular graft fixation. More specifically, the suture bore 161 overlaps with a proximal region of the graft material, thereby allowing a suture to couple the stent 120 to the graft material with some desired degree of overlap. The proximal edge of the graft material therefore may be aligned with the imaging bores 190. Advantageously, a physician may know exactly where the proximal edge of the graft material is being placed because he or she can view the position of the radiopaque markers in the imaging bores 190. Therefore, the chances of inadvertently overlapping the graft material with a branch vessel, or another undesired location, may be reduced.

Figure 8:
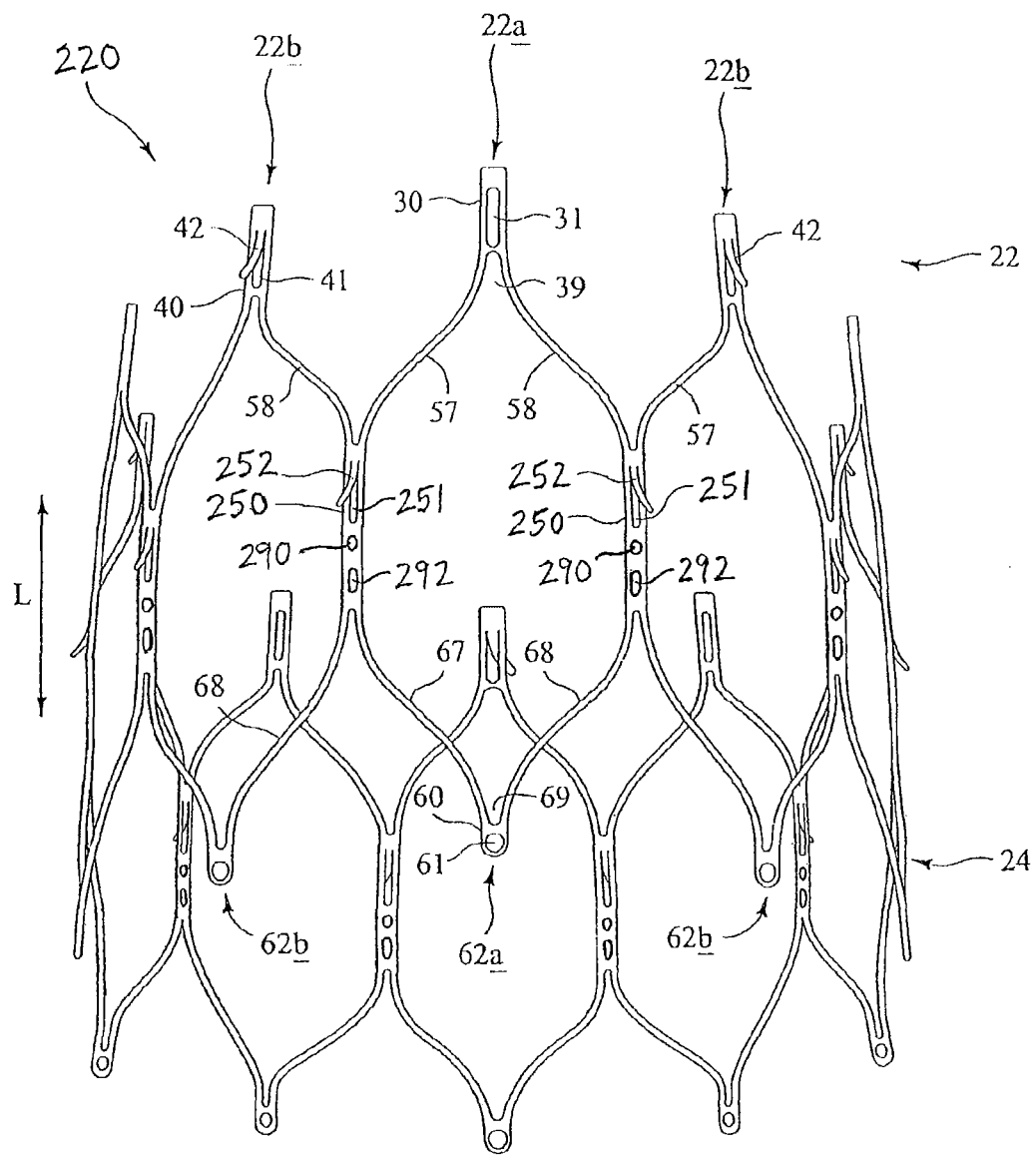
FIG. 8 is a lower perspective view of an alternative embodiment of a cannula-cut stent.
Figure 9:
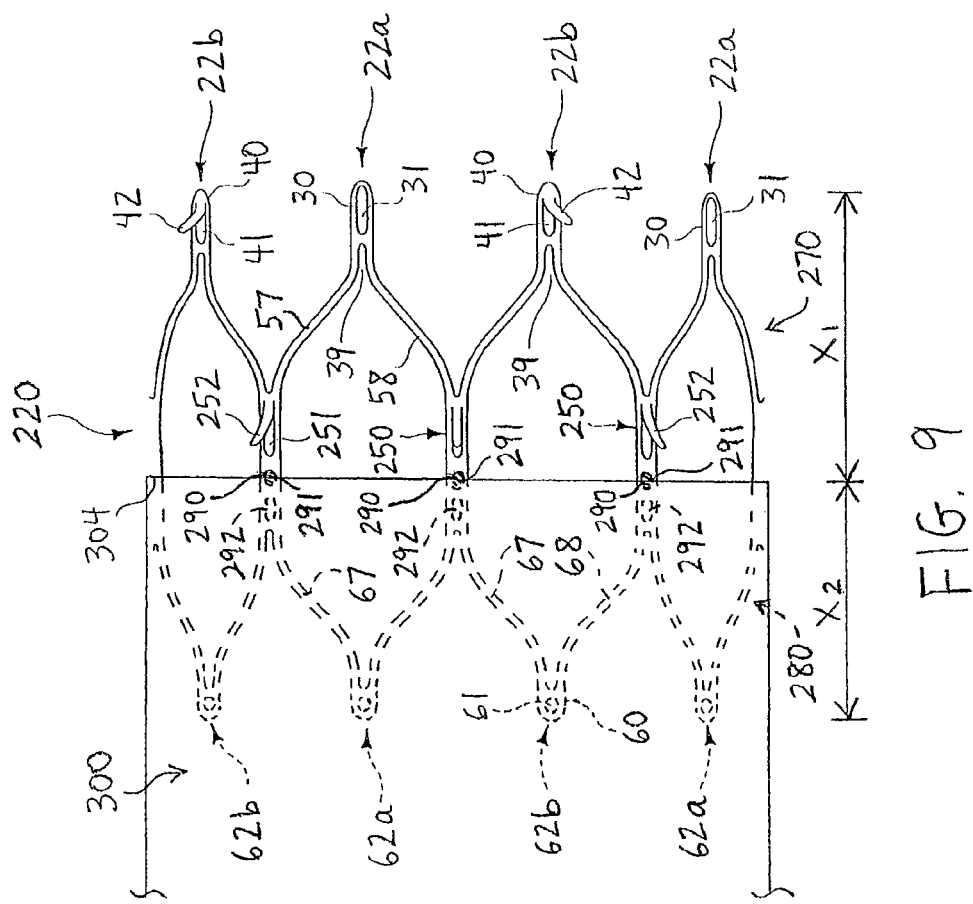
FIG. 9 is a side view of the stent of FIG. 8 coupled to a graft material.

Referring now to FIGS. 8-9, an alternative stent 220 is shown and described. The stent 220 is similar to the stent 20 of FIGS. 1-2, with main exceptions noted below, and reference numbers of the stent 220 correspond to like reference numbers of the stent 20.

The stent 220 comprises a transition region 250, where the first angled strut segments 57 and 67 of the proximal and distal apices 22a and 62a, respectively, may meet with the second angled strut segments 58 and 68 of the adjacent proximal and distal apices 22b and 62b. Like the stent 20 of FIGS. 1-2, the stent 220 comprises at least one barb 252 disposed in at least one of the transition regions 250. As noted above with regard to the transition regions 50, the barb 252 of the transition regions 250 may be formed integrally, as part of the strut, or may comprise an external barb that is adhered to a surface of the transition regions 250. Preferably, as shown in FIG. 1, multiple integral barbs 252 are provided, e.g., by laser cutting a desired barb shape and forming slits 251 into the transition regions 250.

Additionally, the transition regions 250 of FIGS. 8-9 comprise an imaging bore 290 and a first suture bore 292. The imaging bore 290 of the transition region 250 is disposed distal to the barb 252, and in turn, the first suture bore 292 is disposed distal to the imaging bore 290, as shown in FIGS. 8-9.

Like the imaging bore 190 described in FIG. 7 above, the imaging bore 290 may receive any suitable radiopaque marker, such as an imaging element 291, e.g., in the form of a gold marker, as depicted in FIG. 9. The imaging bores 290 with the imaging element 291 disposed therein align with a proximal edge 304 of a graft material 300, as shown in FIG. 9, thereby allowing for precise imaging of the proximal edge 304. Preferably, the imaging bores 290 and associated imaging elements 291 are provided on each of the transition regions 250, as shown in FIGS. 8-9. Therefore, in the example of FIGS. 8-9 where ten different transition regions 250 are provided between the proximal and distal apices, then ten different imaging bore 290 and corresponding imaging elements 291 are provided at the proximal edge 304 of the graft material 300, thereby allowing for significantly enhanced visualization at the proximal edge 304, particularly when the stent 220 is used for endovascular graft fixation.

The first suture bore 292 overlaps with a proximal region of the graft material 300, thereby allowing a suture to couple the stent 220 to the graft material 300 with some desired degree of overlap. The proximal edge 304 of the graft material 300 therefore may be aligned with the imaging bores 290, as noted above.

In the embodiment of FIGS. 8-9, due to the provision of the first suture bore 292 in the transition region 250, the bore 61 formed in the end region 60 of the distal apices 62a and 62b becomes a second suture bore. In other words, the graft material 300 is secured to the stent 220 via a suture disposed through the first suture bore 292, and additionally is secured to the stent 220 via a suture disposed through the second suture bore 61. A distal portion of the stent 220 therefore is secured to the graft material 300 at multiple spaced-apart longitudinal positions.

In the embodiment of FIGS. 8-9, the stent 220 overlaps with the graft material 300 in a manner such that the stent 220 is capable of performing functions previously performed by two separate stents. Specifically, the design of the stent 220 and its manner of overlap with the graft material 300 allows the stent 220 to perform both a sealing function for the proximal end of the graft material 300, and additionally to perform a bare attachment function to a vessel.

In particular, the stent 220 comprises a proximal region 270, including the series of proximal apices 22a and 22b and a proximal portion of the transition region 250 including the at least one barb 252, which spans a length $x_1$ and is disposed proximally beyond the graft material 300, as shown in FIG. 9. The stent 220 also comprises a distal region 280 including the series of distal apices 62a and 62b and a distal portion of the transition region 250 including the first suture bore 292, which spans a length $x_2$ and overlaps with the graft material 300. Notably, the imaging bore 290 with the corresponding imaging element 291 is disposed at a location corresponding to an endpoint of the proximal edge 304 of the graft material 300.

In one embodiment, the length $x_1$ of the proximal region 270 of the stent 220 that disposed proximally beyond the graft material 300 accounts for between about 55 to about 80 percent of the longitudinal length of the stent 220, while the length $x_2$ of distal region 280 of the stent that disposed within the graft material 300 accounts for between about 20 to about 45 percent of the longitudinal length of the stent.

Advantageously, the proximal region 270 of the stent 220 may be used as an attachment stent portion for endovascular graft fixation, while the distal region 280 of the stent 220 overlaps with the graft material 300 a sufficient distance to perform a sealing function for the proximal end of the graft 300. This eliminates the need to provide a first stent at the proximal end of the graft material to provide a sealing function for the graft material 300 and a separate, substantially bare second stent attached at the most proximal end of the graft material 300 and extending proximally therefrom to perform an endovascular fixation function.

The stent 220 of FIGS. 8-9, which eliminates the need for separate proximal graft sealing and bare vessel attachment stents, is particularly suitable and advantageous in treatment of thoracic or abdominal aortic aneurysms where there is a compromised anatomy allowing for a relatively short stent attachment zone at a proximal location. The stent 220 may be used with neck lengths (i.e., a sealing zone of the healthy tissue disposed between compromised tissue and/or side vessels) of between about 10 mm to about 15 mm. The stent 220 also may be used with neck angles up to about 45 degrees when disposed superior to the renal arteries and neck lengths up to about 60 degrees when disposed inferior to the renal arteries. The stent 220, when overlapping the proximal end of a graft material 300 as shown, therefore is able to "land" in a neck region of a patient's anatomy that is relatively short and angled, and where previous devices that utilized two separate stents at the proximal end of a graft material could not "land" without overlapping compromised tissue and/or side vessels. Additionally, the stent 220, providing both graft sealing and bare attachment functions, may provide a higher radial force upon a vessel relative to separate sealing and bare attachment stents.

In one embodiment, the graft material 300 may comprise one or more stents coupled to distal and central regions of the graft material 300, i.e., at locations distal to the stent 220. The one or more stents coupled to distal and central regions of the graft material 300 may comprise a zig-zag shape formed from a single bent wire, or other desired shapes, thereby maintaining patency along a longitudinal length of the graft material 300 at locations distal to the stent 220.

Figure 10:
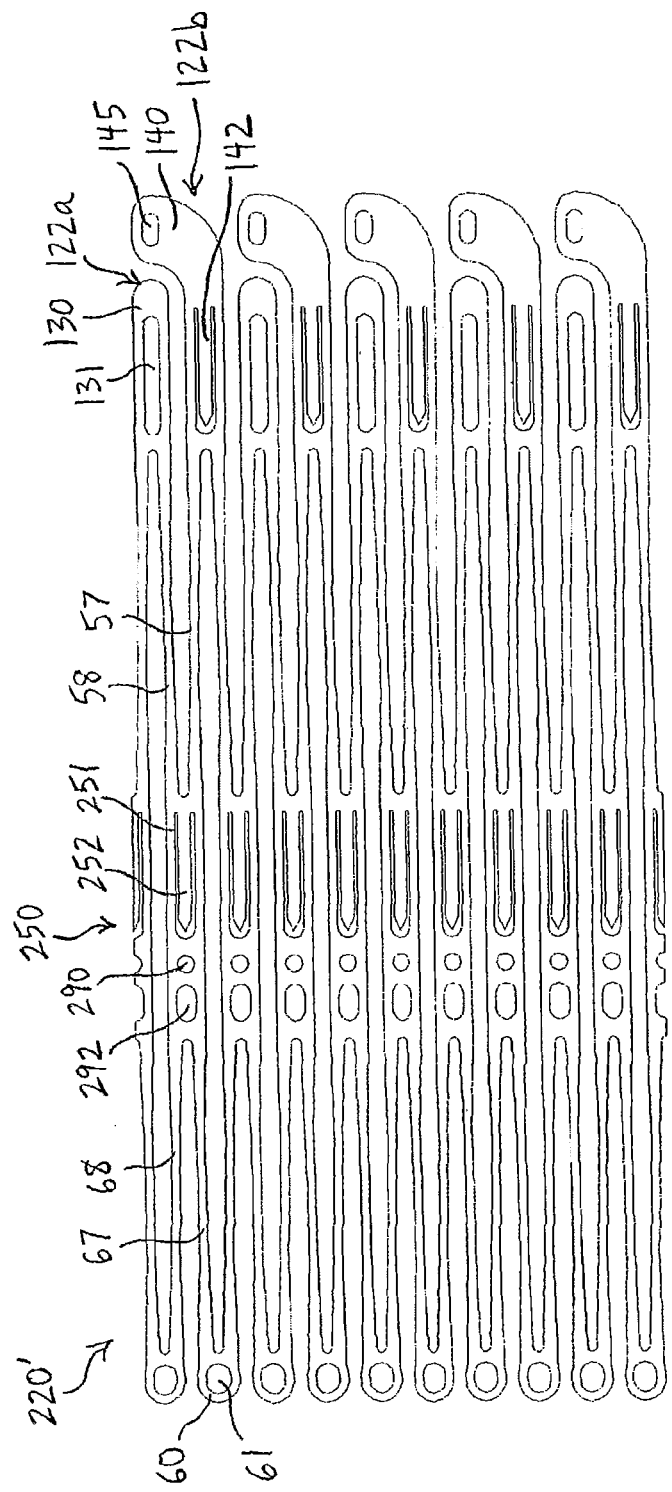
FIG. 10 is a side view of an alternative stent in a flattened configuration.

Referring now to FIG. 10, an alternative stent 220' is similar to the stent 220 of FIGS. 8-9, with a main exception that the proximal region of the stent 220' comprises the alternating proximal apices 122a and 122b of FIGS. 3-6. Thus, the stent 220' of FIG. 10, like the stent 120 of FIGS. 3-6 above, permits a single trigger wire 184 to be disposed through the first and second bores 131 and 145 of adjacent proximal apices 122a and 122b, respectively.

Figure 11:
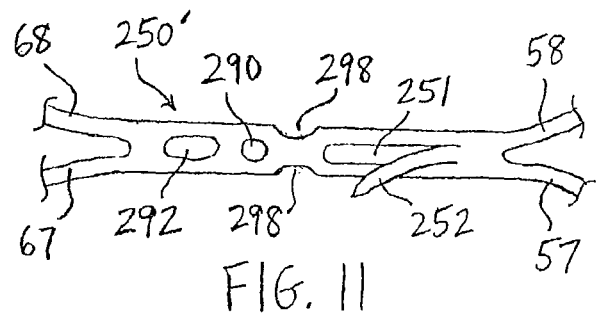
FIG. 11 is a side view of a transition region of an alternative stent.

Referring now to FIG. 11, in an alternative embodiment, the stents 220 or 220' of FIGS. 8-10 may further comprising a notched region 298 of reduced diameter disposed in an alternative transition region 250' between the imaging bore 290 and the at least one barb 252. The notched region 98 facilitates radial flaring of the proximal region 270 of the stents 220 and 220', thereby allowing the proximal apices to securely engage a vessel wall. While an exemplary notched region 298 is shown in FIG. 11, alternative structures may be used to promote flaring of the proximal 270 radially outward relative to the distal region 280.

Figure 12:
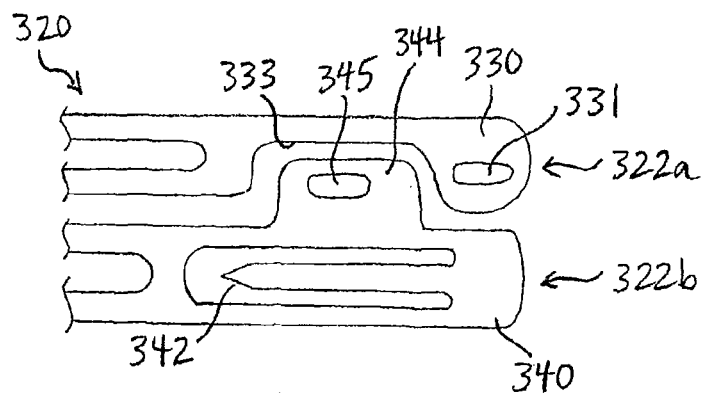
FIG. 12 is a side view illustrating features of proximal apices of an alternative stent.
Figure 13:
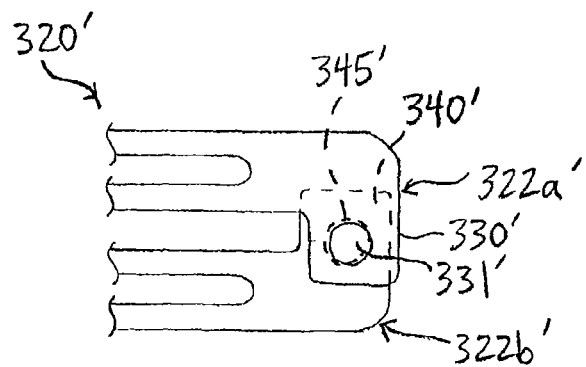
FIG. 13 is a side view illustrating features of proximal apices of a further alternative stent.

Referring now to FIGS. 12-13, alternative arrangements of proximal apices of a stent 320, which may reduce the number of trigger wires in accordance with the principles above, are shown and described. In FIG. 12, one or more pairs of adjacent, proximal apices 322a and 322b may comprise different features. For example, a first proximal apex 322a may comprise an end region 330 having a first bore 331 formed therein, wherein the first bore 331 is configured to receive the trigger wire 184 of FIGS. 5-6 above. A second, adjacent proximal apex 322b comprises an end region 340 having an integral barb 342 formed therein, as shown in FIG. 12. The second proximal apex 322b further comprises a protruding region 344 having a second bore 345 formed therein, which is configured to receive the same trigger wire 184 as the adjacent first proximal apex 322a, in the manner described and shown with respect to FIGS. 5-6 above.

The first proximal apices 322a further may comprise a recessed portion 333 formed at a location distal to the first bore 331, as shown in FIG. 12. During delivery of the stent 320, the second proximal apex 322b is configured to be pulled towards the first proximal apex 322a, such that the protruding region 344 of the second proximal apex 322b may become nested within the recessed portion 333 of the first proximal apex 322a when the trigger wire 184 of FIGS. 5-6 is disposed through the first and second bores 331 and 345. The first and second bores 331 and 345 are disposed substantially in longitudinal alignment with one another when the single trigger wire 184 is disposed through the first and second bores 331 and 345 during delivery of the stent. Advantageously, by using adjacent proximal apices 322a and 322b having the different features shown herein, an improved trigger wire attachment may be achieved and barb entanglement may be reduced, as explained above.

Referring to FIG. 13, a stent 320' having one or more pairs of adjacent proximal apices 322a' and 322b' may comprise generally symmetrical features. The proximal apices 322a' comprise an end region 330' having a first bore 331' formed therein, while the distal apices 322b' comprise an end region 340' having a second bore 345' formed therein. The end regions 330' and 340' comprise protrusions, in which the first and second bores 331' and 345' are disposed, and where the protrusions generally face each other. Therefore, during delivery of the stent 320', the second proximal apex 322b' is configured to be pulled towards the first proximal apex 322a', such that the protrusions of the first and second proximal apices 322a' and 322b' overlap, and in turn, the first and second bores 331' and 345' directly overlap as shown in FIG. 13. Therefore, the trigger wire 184 of FIGS. 5-6 may be disposed through the first and second bores 331' and 345'.

Figure 14:
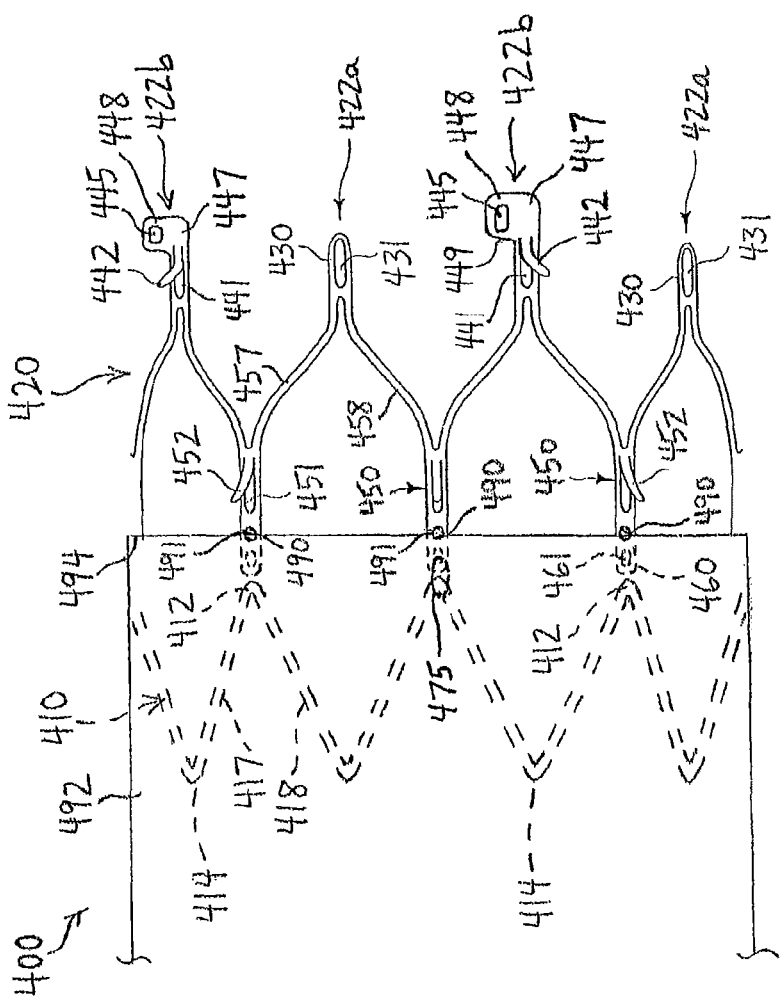
FIG. 14 is of an embodiment of a stent-graft including first and second stents.
Figure 15:
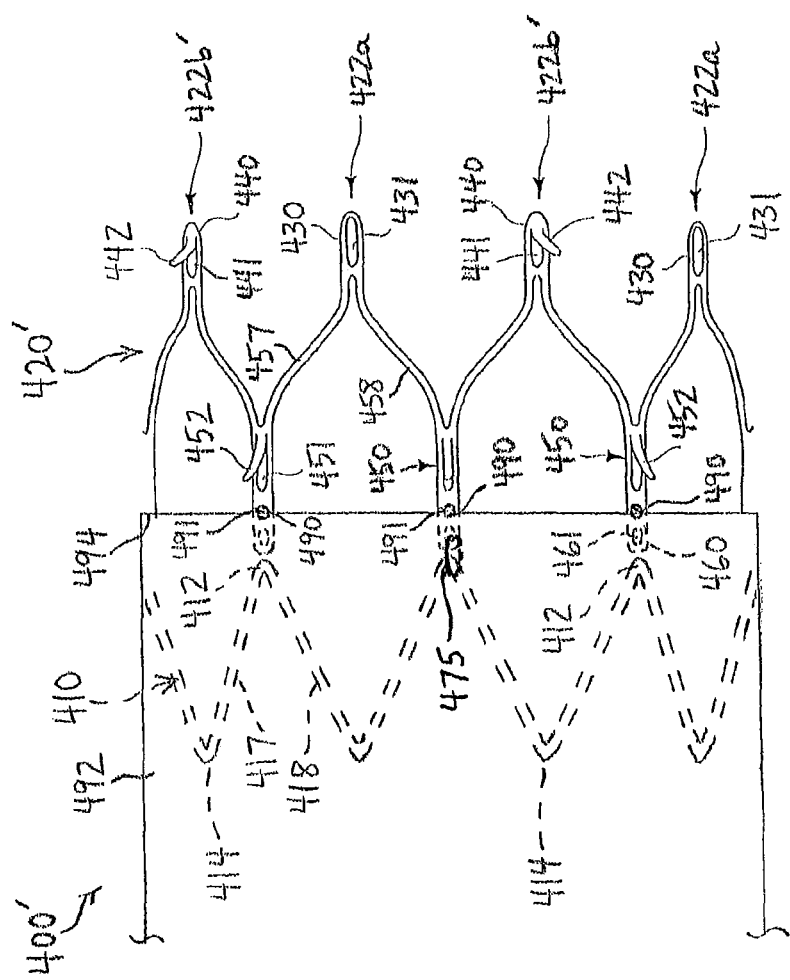
FIG. 15 is an alternative embodiment of the stent-graft of FIG. 14.

Referring now to FIGS. 14-15, alternative embodiments are shown and described. In FIG. 14, stent-graft 400 comprises first and second stents 410 and 420 and a graft 492. The graft 492 has proximal and distal ends and a lumen extending therebetween, though for illustrative purposes only the proximal end 494 of the graft 492 is shown in FIGS. 14-15.

The first stent 410 has proximal and distal ends, a series of proximal apices 412 disposed at the proximal end of the first stent 410, a series of distal apices 414 disposed at the distal end of the first stent 410. A plurality of strut segments 417 and 418 are disposed between the series of proximal apices 412 and the series of distal apices 414 of the first stent 410, as shown in FIGS. 14-15. The first stent 410 overlaps with the graft 492 along a longitudinal length between the proximal and distal ends of the first stent 410, such that the series of proximal apices 412 of the first stent 410 are each disposed distal to the proximal end 494 of the graft 492, as shown in FIGS. 14-15.

The second stent 420 has proximal and distal ends, a series of proximal apices 422a and 422b disposed at the proximal end of the second stent 420, and a series of distal apices 460 disposed at the distal end of the second stent 420. A plurality of strut segments 457 and 458 are disposed between the series of proximal apices 422a and 422b and the series of distal apices 460 of the second stent 420, as shown in FIGS. 14-15. The series of distal apices 460 of the second stent 420 are each disposed distal to the proximal end 494 of the graft 492, and the series of proximal apices 422a and 422b of the second stent 420 are each disposed proximally beyond the proximal end 494 of the graft 492.

At least one of the proximal apices 412 of the first stent 410 may be circumferentially aligned with a corresponding distal apex 460 of the second stent 420. In one embodiment, each of the proximal apices 412 of the first stent 410 is circumferentially aligned with a corresponding distal apex 460 of the second stent 420, as depicted in FIGS. 14-15.

At least one of the proximal apices 412 of the first stent 410 may be coupled to one of the distal apices 460 of the second stent 420 by a suture 475, as shown in FIGS. 14-15. In one embodiment, each of the proximal apices 412 of the first stent 410 is sutured to a corresponding one of the distal apices 460 of the second stent 420 using a suture 475. The suture 475 may be disposed through a portion of the graft 492, thereby simultaneously coupling one of the proximal apices 412 of the first stent 410 to one of the distal apices 460 of the second stent 420 and also to the graft 492. If desired, multiple sutures 475 may be used to couple the adjacent stents together, or one suture 475 may be used to couple the adjacent stents together while one or more separate sutures are used to couple the stents 410 and 420 to the graft 492.

In the embodiment of FIGS. 14-15, the first stent 410 and the second stent 420 may comprise different geometries. In a non-limiting example, the first stent 410 comprises a zig-zag stent shape as shown in FIGS. 14-15. In contrast, the second stent 420 of FIG. 14 has features of a stent that are similar to those described with respect to the stent 120 of FIGS. 3-6 above. In particular, the second stent 420 has a plurality of alternating first and second proximal apices 422a and 422b, where each of the first proximal apices 422a comprises an end region 430 having a first bore 431. Each of the second proximal apices 422b may comprise first and second regions 447 and 448, as shown in FIG. 14. A single barb 442 may be disposed in each of the second proximal apices 422b generally in the first region 447, while a second bore 445 may be disposed generally in the second region 448, as shown in FIG. 14. The barbs 442 may be formed by laser cutting a desired barb shape into the end regions, thereby forming a slit 441, as generally explained with respect to the stent 120 hereinabove. Once the desired barb shape is cut, a main body of the barb 442 may be bent in a radially outward direction and optionally may be sharpened, as generally set forth above. The second proximal apices 422b further may comprise a recessed portion 449 formed at a location distal to the second bore 445. As generally explained above with respect to the embodiment of FIGS. 3-6, during delivery of the stent 420, the first proximal apex 422a is configured to be pulled towards the second proximal apex 422b and may become nested within the recessed portion 449 of the second proximal apex 422b when a trigger wire is disposed through the first and second bores 431 and 445.

The first and second angled strut segments 457 and 458 meet with one another distally to form a distal transition region 450. In the embodiment of FIGS. 14-15, each of the distal apices 460 of the second stent 420 comprises a suture bore 461 adapted to receive a suture for coupling the distal end of the second stent 420 to the graft 492. Further, the suture bore 461 may be used to couple the distal end of the second stent 420 to the proximal end of the first stent 410 via a suture 475, as noted above.

Further, each of the distal apices 460 of the second stent 420 may comprise an imaging bore 490 adapted to receive a radiopaque marker 491. As described with respect to the embodiment of FIGS. 7 and 9 above, the imaging bore 490 is disposed proximal to the suture bore 461, and the imaging bore 490 is adapted to be aligned with the proximal end 494 of the graft 492, thereby allowing the imaging element 491 associated with the imaging bore 490 to significantly enhance imaging directly at the proximal end 494 of the graft 492. Further, the second stent 420 may comprises at least one barb 452 that is integrally formed along the distal transition region 450.

In FIG. 15, an alternative stent-graft 400' is similar to the stent-graft 400 of FIG. 14, with a main exception that an alternative second stent 420' comprises alternating first and second proximal apices 422a and 422b'. Each of the first proximal apices 422a comprises the end region 430 having the bore 431 as described in FIG. 14, while each of the second proximal apices 422b' comprises at least one barb 442 for engaging tissue in a manner described above with respect to the embodiment of FIGS. 1-2.

In each of the embodiments of FIGS. 14-15, by having separate first and second stents 410 and 420, bending and flexibility along the proximal region of the device may be enhanced while not compromising sealing and attachment functions. It has been unexpectedly found that by placing adjacent stents 410 and 420 in the manner shown in FIGS. 14-15, particularly with one or more apices aligned with one another, that the flexibility of the stents relative to one another can be increased as opposed to decreased. The use of a suture 475 to couple apices of adjacent stents together may further provide an increased flexibility of the adjacent stents 410 and 420 relative to one another. Accordingly, due to the enhanced flexibility in the embodiments of FIGS. 14-15, the stent-grafts 400 and 400' may be useful for accommodating highly angulated and shorter aneurysm necks, thereby increasing the number of patients that can be treated. Moreover, the designs of FIGS. 14-15 are expected to reduce infolding along the proximal region of the device and promote enhanced stability when positioned within a bodily lumen.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A stent for use in a medical procedure, the stent comprising:
   a series of proximal apices disposed at a proximal end of the stent;
   a series of distal apices disposed at a distal end of the stent;
   a plurality of strut segments disposed between each proximal apex and each distal apex, where the strut segments enable expansion of the stent from a compressed state to a deployed state, and where adjacent strut segments are joined at a transition region between the proximal and distal apices;
   an imaging bore formed in the transition region; and
   a first suture bore formed in the transition region and disposed distal to the imaging bore, the first suture bore adapted to receive a suture for coupling a portion of the transition region to a graft material,
   where a distal region of the stent, including the series of distal apices and a distal portion of the transition region including the first suture bore, overlaps with the graft material,
   where a proximal region of the stent, including the series of proximal apices and a proximal portion of the transition region including at least one barb, is disposed proximally beyond the graft material, and
   where the imaging bore is disposed at the location corresponding to an endpoint of a proximal edge of the graft material.

2. The stent of claim 1 where the distal region of the stent that overlaps with the graft material accounts comprises about 20 to about 45 percent of the longitudinal length of the stent, while the proximal region of the stent that is disposed distally beyond the graft material comprises between about 55 to about 80 percent of the longitudinal length of the stent.

3. The stent of claim 1 further comprising a notched region of reduced diameter disposed in the transition region at a location proximal to the imaging bore and the at least one barb, where the notched region facilitates radial flaring of the proximal region of the stent.

4. The stent of claim 1 where the series of proximal apices comprises alternating first and second proximal apices, where each of the first proximal apices comprises an end region having a first bore, and where each of the second proximal apices comprises a second bore,
   where at least one of the first proximal apices is simultaneously restrained with an adjacent, second proximal apex by a single trigger wire disposed through the first and second bores during delivery of the stent.

5. The stent of claim 4 where the second proximal apex comprises at least one integral barb disposed adjacent to the second bore.

6. The stent of claim 4 where the first bore formed in the first proximal apex directly overlaps longitudinally and circumferentially with the second bore in the second proximal apex in a delivery state.

7. The stent of claim 4 further comprising a recessed portion formed in the first proximal apex at a location distal to the first bore, where the second proximal apex is configured to be pulled towards the first proximal apex to become nested within the recessed portion of the first proximal apex, where the first and second bores are disposed substantially in longitudinal alignment with one another when the single trigger wire is disposed through the first and second bores during delivery of the stent.

8. A stent for use in a medical procedure, the stent comprising:
- a series of proximal apices disposed at a proximal end of the stent;
- a series of distal apices disposed at a distal end of the stent;
- at least one imaging element disposed between the series of proximal apices and the series of distal apices; and
- a first suture bore disposed in a surface of the stent at a location distal to the imaging element, the first suture bore adapted to receive a suture for coupling a portion of the stent to a graft material,
- where a distal region of the stent, including the series of distal apices and the first suture bore, overlaps with the graft material,
- where a proximal region of the stent, including the series of proximal apices and at least one barb, is disposed proximally beyond the graft material,
- where the distal region of the stent that overlaps with the graft material comprises between about 20 to about 45 percent of the longitudinal length of the stent, while the proximal region that is disposed distally beyond the graft material comprises between about 55 to about 80 percent of the longitudinal length of the stent.

9. The stent of claim 8 where the imaging element is disposed at a location corresponding to an endpoint of a proximal edge of the graft material.

10. The stent of claim 8 where each of the distal apices comprises an end region having a second suture bore adapted to receive a suture for coupling the distal apices to the graft material.

11. A stent-graft for use in a medical procedure, the stent-graft comprising:
- a graft having proximal and distal ends and a lumen extending therebetween;
- a first stent having proximal and distal ends, a series of proximal apices disposed at the proximal end of the first stent, a series of distal apices disposed at the distal end of the first stent, and a plurality of strut segments disposed between the series of proximal apices and the series of distal apices of the first stent, where the series of proximal apices of the first stent are each disposed distal to the proximal end of the graft; and
- a second stent having proximal and distal ends, a series of proximal apices disposed at the proximal end of the second stent, and a series of distal apices disposed at the distal end of the second stent, and a plurality of strut segments disposed between the series of proximal apices and the series of distal apices of the second stent, where the series of distal apices of the second stent are each disposed distal to the proximal end of the graft, and where the series of proximal apices of the second stent are each disposed proximally beyond the proximal end of the graft,
- where at least one of the proximal apices of the first stent is circumferentially aligned with a corresponding distal apex of the second stent, and
- where the first stent and the second stent comprise different geometries.

12. The stent-graft of claim 11 where at least one of the proximal apices of the first stent is sutured to one of the distal apices of the second stent.

13. The stent-graft of claim 11 where:
the first stent comprises a zig-zag stent shape; and
the series of proximal apices of the second stent comprises a plurality of alternating first and second proximal apices, where each of the first proximal apices comprises an end region having a first bore, and where each of the second proximal apices comprises first and second regions, where at least one integral barb is formed in the first region and where a second bore is formed in the second region, and each of the second proximal apices further comprises a recessed portion formed in the second proximal apex at a location distal to the second bore, where at least one of the first proximal apices is nested within the recessed portion of an adjacent, second proximal apex delivery of the stent.

14. The stent-graft of claim 11 where each of the distal apices of the second stent comprises a suture bore adapted to receive a suture for coupling a distal end of the second stent to the graft.

15. The stent-graft of claim 14 where each of the distal apices of the second stent further comprises an imaging bore adapted to receive a radiopaque marker, where the imaging bore is disposed proximal to the suture bore, and the imaging bore is adapted to be aligned with the proximal edge of the graft.

* * * * *